United States Patent [19]

Policello

[11] Patent Number: 5,104,647
[45] Date of Patent: Apr. 14, 1992

[54] SURFACTANT BLEND OF ORGANOSILICONE AND POLYALKYLENE OXIDE POLYMERS USEFUL AS AN AGRICULTURAL ADJUVANT

[75] Inventor: George A. Policello, Peekskill, N.Y.

[73] Assignee: Union Carbide Chemicals & Plastics Technology Corporation, Danbury, Conn.

[21] Appl. No.: 541,958

[22] Filed: Jun. 22, 1990

[51] Int. Cl.$^5$ .................. C08L 71/02; C08L 83/12; A01N 25/30; A01N 25/02
[52] U.S. Cl. ......................... 514/772; 424/407; 424/486; 523/122; 525/403; 71/64.1
[58] Field of Search ................ 424/78; 525/403

[56] References Cited

U.S. PATENT DOCUMENTS

| | | | |
|---|---|---|---|
| 3,562,786 | 2/1971 | Bailey et al. | 252/137 |
| 4,347,330 | 8/1982 | Demou et al. | 521/110 |
| 4,818,421 | 4/1989 | Boris et al. | 528/29 |
| 4,933,002 | 6/1990 | Petroff et al. | 71/116 |
| 4,942,034 | 7/1990 | Hill et al. | 424/443 |

FOREIGN PATENT DOCUMENTS 8912394 12/1989 PCT Int'l Appl.

OTHER PUBLICATIONS

D. R. Leece et al., Comparison of Urea Foliar Sprays Containing Hydrocarbon or Silicone Surfactants with Soil-Applied Nitrogen in Maintaining the Leaf Nitrogen Concentration of Prune Trees, J. Amer. Soc. Hort. Sci. 104(5):644-648 (1979).

M. J. Rosen. Phenomena in Mixed Surfactant Systems, (J. F. Scamehorn, Ed.) ACS Symp. Ser., vol. 311, p. 144 (1986).

R. J. Field et al., Promotion of Stomatal Infiltration of Glyphosate by an Organosilicone Surfactant Reduces the Critical Rainfall Period. Pestic. Sci. 1988, 24, 55-62.

C. W. Coggins et al., Possible Methods to Increase Efficacy of Gibberellic Acid Applied Preharvest to Naval Orange Trees, Second International Symposium on Adjuvants for Agrichemicals Jul. 31-Aug. 3, 1989.

J. A. Zabkiewicz et al., Effect of Addivitives on Foliar Wetting and Uptake of Glyphosate into Gorse, 1985 BCPC Monograph No. 28 Symposium on Application and Biology, pp. 127-134.

J. M. Balneaves, The Effect of Added Surfactant on the Performance of Scrubweed Herbicides, Proc. 38th N.Z. Weed and Pest Control Conf.

D. N. Rubingh et al., Mechanism of Detergency in Systems Containing Cationic and Monionic Surfactants, Ind. Eng. Chem. Prod. Res. Dev., vol. 21, No. 2, 1982.

Primary Examiner—Thurman K. Page
Assistant Examiner—E. J. Webman
Attorney, Agent, or Firm—Bonnie L. Deppenbrock

[57] ABSTRACT

A surfactant mixture for use as a pesticide adjuvant comprising an organosilicone compound and a polyalkyleneoxide copolymer.

5 Claims, 8 Drawing Sheets

SURFACTANT BLEND OF ORGANOSILICONE AND POLYALKYLENE OXIDE POLYMERS USEFUL AS AN AGRICULTURAL ADJUVANT

BACKGROUND OF THE INVENTION

1. Field of the Invention

The present invention generally relates to surfactant blends and their use as adjuvants in applications for dispersing, wetting and spreading pesticides. More particularly, the present invention relates to blends of an organosilicone compound and a polyalkyleneoxide copolymer for use in such applications.

2. Prior Art

Nonionic surfactants are commonly used in forestry and horticulture as agricultural adjuvants to improve the efficacy of pesticides such as micronutrients, biologicals, herbicides, fungicides and growth regulators. Surfactants play several roles in this application, including dispersings, wetting, spreading and emulsifying, either as part of the formulated product or as a tank side post-add.

Nonionic surfactants are well known for their ability to reduce the surface tension of aqueous solutions. This reduction in surface tension is important for the spreading of solutions on difficult to wet surfaces, such as a waxy leaf cuticle. Surfactants aid in the uptake of active ingredients into the plant tissue through permeation of the cuticle, through defects in the surface, and in some special cases, through flooding of the leaf stomata. Although conventional nonionic surfactants enhance the wetting of spray formulations they do not provide total wetting on hydrophobic leaf surfaces. This can result in poor uptake of active ingredients and a low degree of rainfast efficacy.

Recently, organosilicone compounds have drawn attention as agricultural adjuvants because of their unique wetting properties. Zabkiewicz, J. A. Gaskin, R. E. and Balneaves, J. M., 1985. Effect of Additives on Foliar Wetting and Uptake of Glyphosate into Gorse. pp. 127–134. In: Application and Biology (BCPC Monograph No. 28) ED: Southcombe, E.S.E. BCPC, 2a Kidderminester Rd, Croydon, CRO 2UE, U.K. ISBN 0-9014368-7-9. These surfactants give surface tension values significantly lower than conventional nonionic surfactants (21 dynes/cm vs 30 dynes/cm). It has been demonstrated by Zabkiewicz et al. some select organosilicone surfactants provide a significant increase in the foliar uptake of herbicide into gorse, when compared to conventional wetting agents.

Also, these spreading of aqueous solutions of the organosilicone compounds give total wetting (as measured by contact angles) on leaf surfaces, while conventional organics give significantly higher contact angles.

The interaction for a variety of surfactant pairs is well documented in the open literature. D. N. Rubingh, 1982, Mechanism of Detergency in Systems Containing Cationic and Nonionic Surfactants, Ind. Eng. Chem. Prod. Res. Dev., 21, 176–182 demonstrated that a reduction in the critical micelle concentration as well as a reduction in surface tension is observed for a variety of surfactant pairs. Rosen, Molecular Interaction and Synergism in Binary Mixtures of Surfactants, ACS Symp. Ser., Vol. 311, page 144 (1986) further showed that interactions between nonionic organic and ionic organic surfactant pairs demonstrate surface tensions lower than would be expected for mixtures of the two organic surfactants (non-ideal behavior). However, the degree of interaction for nonionic/nonionic surfactant pairs was limited. Generally, Rosen supports the belief that these surfactant pairs display ideal solution behavior.

The prior art described by Rosen, and Rubingh deal with interactions between organic surfactant pairs. The interactions for nonionic/nonionic surfactant pairs is limited while the present invention demonstrates significant and unexpected interaction between a nonionic polyalkyleneoxide copolymer and a nonionic organosilicone compound.

U.S. Pat. No. 3,562,786 (Bailey) described mixtures of nonionic organosilicone compounds with conventional organic nonionic and ionic surfactants. The organosilicone compound is claimed to be useful in lowering the aqueous surface tension of organic surfactant solutions.

The nonionic surfactants described by Bailey deal primarily with nonylphenol or alcohol ethoxylates. These materials, when used as a cosurfactant for the organosilicone compounds described in this invention, interfere with the spreading characteristics of the organosilicone compounds. The present invention describes a specific synergistic surfactant composition, where the organic cosurfactant does not interfere with wetting or spreading of the organosilicone compound.

OBJECTS OF THE INVENTION

It is an object of this invention to provide a surfactant mixture that will have spreading characteristics similar to that obtained from an organosilicone compound alone.

It is another object of this invention to provide a surfactant mixture that gives improved dynamic and equilibrium surface tension values when compared to the individual components of the mixture.

Other objects and advantages will be apparent from the description and examples which follow.

BRIEF DESCRIPTION OF THE FIGURES

FIGS. 1, 2 and 3 are from Example 1. FIG. 5, 6, 7 and 8 are from Example 2.

SUMMARY OF THE INVENTION

The present invention provides an improved surfactant blend and its use as an agricultural adjuvant. The surfactant blend comprises an organosilicone compound mixed with a polyalkylene-oxide copolymer. This surfactant blend allows for good dispersions and surface tension without sacrificing the spreading efficacy of the mixture. The surfactant blend is especially useful in agricultural applications as an adjuvant for the delivery of pesticides such as micronutrients, biologicals, herbicides, fungicides and growth regulators.

DETAILED DESCRIPTION OF THE INVENTION

In accordance with the present invention there is provided a surfactant blend which comprises a mixture of an organosilicone compound and a polyalkyleneoxide copolymer.

The organosilicone compound is of the general formula:

$$MD_yD'_xM \qquad (I)$$

wherein:

$M = Me_3SiO_{\frac{1}{2}}$
$D = Me_2SiO$
$D' = MeRSiO$
$Me = CH_3$
$R = C_nH_{2n}O(C_2H_4O)_a(C_3H_6O)_bR'$ wherein n is from 2 to 4, preferably 3; a is 3 to 25, preferably 3 to 15, and b is from 0 to 25, preferably 0 to 15; it being understood that the oxyalkylene groups may be random and/or block mixtures of oxyalkylene units.

$R'$ = hydrogen, an alkyl group having 1 to 4 carbon atoms, or an alkyl ester group wherein the alkyl group of the ester has 1 to 4 carbon atoms. Each $R'$ can be same or different on any given molecule. Preferably $R'$ is hydrogen or methyl.

$Y = 0$ to 5, preferably zero.

$x = 1$ to 5, preferably 1.

The polyalkyleneoxide copolymer is of the general formula:

$$R''O\text{-}(C_2H_4O)_c(C_3HO)_d\text{-}R'' \qquad (II)$$

wherein c is 0 to 300, preferably 20 to 100, d is 1 to 300, preferably 20 to 100, it being understood that the oxyalkylene groups may be random and/or block mixtures of oxyalkylene units;

$R''$ = hydrogen or an alkyl group having 1 to 4 carbon atoms, preferably hydrogen.

The polyalkyleneoxide copolymers described above may be either block and/or random.

These polyalkyleneoxide copolymers range in molecular weight from 500 to 15000. A preferred range is 1000 to 8000 and a most preferred range is from 1000 to 3000 molecular weight.

Also, the polyalkyleneoxide copolymers have a preferred range of ethylene oxide (EO) from 10 to 90 weight percent and a most preferred range of 10 to 50 weight percent.

These types of polyalkyleneoxide copolymers are commercially available as Pluronics ™ (from BASF), UCON ™ Fluids (from Union Carbide Chemicals and Plastics Company Inc.) and Poly-Tergents ™ (from Olin Corp.).

The weight fraction of the organosilicone compound in the blend is preferred to be from 1% to 99%. The weight fraction of the polyalkyleneoxide copolymer is preferred to be from 1% to 99%. The most preferred range for the organosilicone compound is from 1% to 50%. and the polyalkyleneoxide copolymer is from 50% to 99%.

The surfactant blends of the present invention find particular utility as adjuvants for dispersing, wetting and spreading pesticides. In particular, the use of these surfactant blends have been found to assist the efficiency of herbicides.

To control weeds, both selective and nonselective herbicides have been employed. The selective herbicides are used when weeds interfere with crop production through competition for water, light, and minerals. If the weeds can be eliminated or greatly reduced with little or no harm to the crop, production is greatly increased.

Nonselective herbicides are used for pre-emergence treatment on farms and around buildings, fences, and the like.

Once a weed population has become established, foliage applications are the most effective means for removal. Success of foliage sprays depends on a number of factors, particularly the nature of the solution and the type of leaf surfaces involved.

Many plants possess a moisture proof waxy coating (cuticle) which prevents excessive loss of water from their foliage. The cuticle is a waxy layer, that is relatively impervious to water. Hence water, does not readily penetrate the leaf surface.

In addition, leaf surfaces are uneven, being ridged or composed of hemispherical cell walls. Water droplets, as of a spray, assume spherical forms with minimum contact surfaces on such a leaf. If the leaf is in a vertical position or if the spray droplet has considerable momentum as it strikes the leaf, an aqueous spray solution may bounce or run off to a large extent.

In many sprays the bulk of the volume is made up of water because it lends driving force to the spray solution. Because of the chemical and physical makeup of the plant surface, aqueous sprays are repelled by most plant surfaces; they round up into spherical droplets and tend to run off. Even when atomized by high pressure and applied with great force, they do not stick to the waxy surfaces of many plants. If they do stick, they stay in place or collect into droplets and present a minimum surface of contact.

The surfactant blends of the present invention have been shown to improve the spreading characteristics of the spray solution, enhance the dynamic and equilibrium surface tension values and assist in dispersing the herbicides.

Illustrative herbicides that could find utility in the present invention include:

3-isopropyl-1H-2,1,3-benzothiadiazin-4(3H)-one 2,2-dioxide;

2-chloro-2'-6'-diethyl-N-(methoxymethyl) acetanilide;

Isoprpylamine salt of N-(phosphonomethyl) glycine;

Fluazifop-butyl-butyl(R S)-2-[4-[[5-(trifluoromethyl)-2-pyrindyl]oxy]phenoxy]propanoate;

1,1'-dimethyl-4-4'-bipyridinium dichloride;

3,4-dichloropropionanilide;

4-amino-3,5,6-trichloropicolinic acid (potassium salt);

4-amino-6-(1,1-dimethylethyl)-3-(methylthio)-1,2,4-triazin-5(4H)-one;

2-[4-[(6-chloro-2-quinoxalinyl)oxy]phenoxy]-propionicacid, ethyl ester;

methyl 2-(((((4-methoxy-6-methyl-methyl 1,3,5-triazin-2-yl)amino) carbonyl)amino) sulfonyl)benzoate;

3,5,6-trichloro-2-pyridinyloxyacetic acid;

4-amino-3,5,6-trichloropicolinic acid; and 3,6-dichloropicolinic acid.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

The surfactants used in the present evaluations are listed below. The organosilicone compound nomenclature used describe the following components:

$M = Me_3SiO_{0.5}$ $D' = MeRSiO$ $Me = CH_3$

| SURFACTANT | STRUCTURAL FORMULA |
|---|---|
| SILICONE 1 | $M D''_x M$ |
| | Where $R = C_3H_6O (C_2H_4O)_{\sim 8}Me$ and $x = 1$ |
| SILICONE 2 | $M D''_x M$ |
| | Where $R = C_3H_6O (C_2H_4O)_{\sim 8}H$ and $x = 1$ |
| SILICONE 3 | $M D''_x M$ |
| | Where $R = C_3H_6O (C_2H_4O)_{\sim 12}H$ and $x = 1$ |
| SILICONE 4 | $M D''_x M$ |
| | Where $R = C_3H_6O (C_2H_4O)_{\sim 5}H$ and $x = 2$ |

| POLYALKYLENEOXIDE SURFACTANTS | | |
|---|---|---|
| SURFACTANT | AVERAGE MOLECULAR WEIGHT | WEIGHT % EO |
| PAO-1 | 1,100 | 10 |
| PAO-2 | 1,900 | 50 |
| PAO-3 | 5,000 | 80 |
| PAO-4 | 2,000 | 10 |
| PAO-5 | 2,500 | 20 |
| PAO-6 | 3,400 | 50 |
| PAO-7 | 8,400 | 80 |
| PAO-8 | 3,600 | 20 |
| PAO-9 | 6,500 | 50 |
| PAO-10 | 14,000 | 80 |
| PAO-11 | 5,000 | 20 |
| PAO-12 | 500 | 50 |
| PAO-13 | 1,900 | 20 |
| PAO-14 | 7,700 | 70 |
| PAO-15 | 12,500 | 70 |

All polyalkyleneoxide copolymers were of general formula II and purchased from BASF except PAO-12 which was purchased from Union Carbide Chemicals and Plastics Company Inc.

| NONIONIC SURFACTANTS | | | |
|---|---|---|---|
| EXAMPLE ID | SURFACTANT | TYPE | WEIGHT % EO |
| NP-7 | TERGITOL ™ NP-7 (a) | NONYLPHENOL ETHOXYLATE | 58 |
| NP-9 | TERGITOL ™ NP-9 (a) | NONYLPHENOL ETHOXYLATE | 64 |
| OP-10 | TRITON ™ X-100 (b) | OCTYLPHENOL ETHOXYLATE | 68 |

(a) Union Carbide Chemicals & Plastics Company
(b) Rohm and Haas Company

EXPERIMENTAL PROCEDURE

The performance of the surfactant mixtures set forth in this invention was evaluated by several methods. Surfactant pair interactions were determined by dynamic surface tension measurements made by the maximum bubble pressure technique. Dynamic surface tension was measured with a SENSEDYNE ™ 6000 surface tensiometer.

The degree of interaction for the surfactant pairs is expressed as the difference between the expected and the observed values for surface tension. Synergy is defined as a reduction in surface tension below that of either of the individual surfactants. Non-ideal mixing is defined as a reduction in surface tension below that of an expected value for a linear relationship between a surfactant pair.

The effect of surfactant pairs on spreading was evaluated by determining the spread ratio of aqueous solutions on a hydrophobic surface. Here, 10 μL of a surfactant solution was applied to a smooth polyester surface. The spread diameter was recorded at 45 seconds. The spreading ratio was calculated by dividing the diameter of a 10 μL drop of distilled water into the diameter of the same volume of surfactant solution.

The surfactant solutions used in all of the above evaluations were prepared in deionized water using a deionization filter from Millipore Corporation. These solutions were freshly prepared before each evaluation.

EXAMPLE 1

Figure 1:
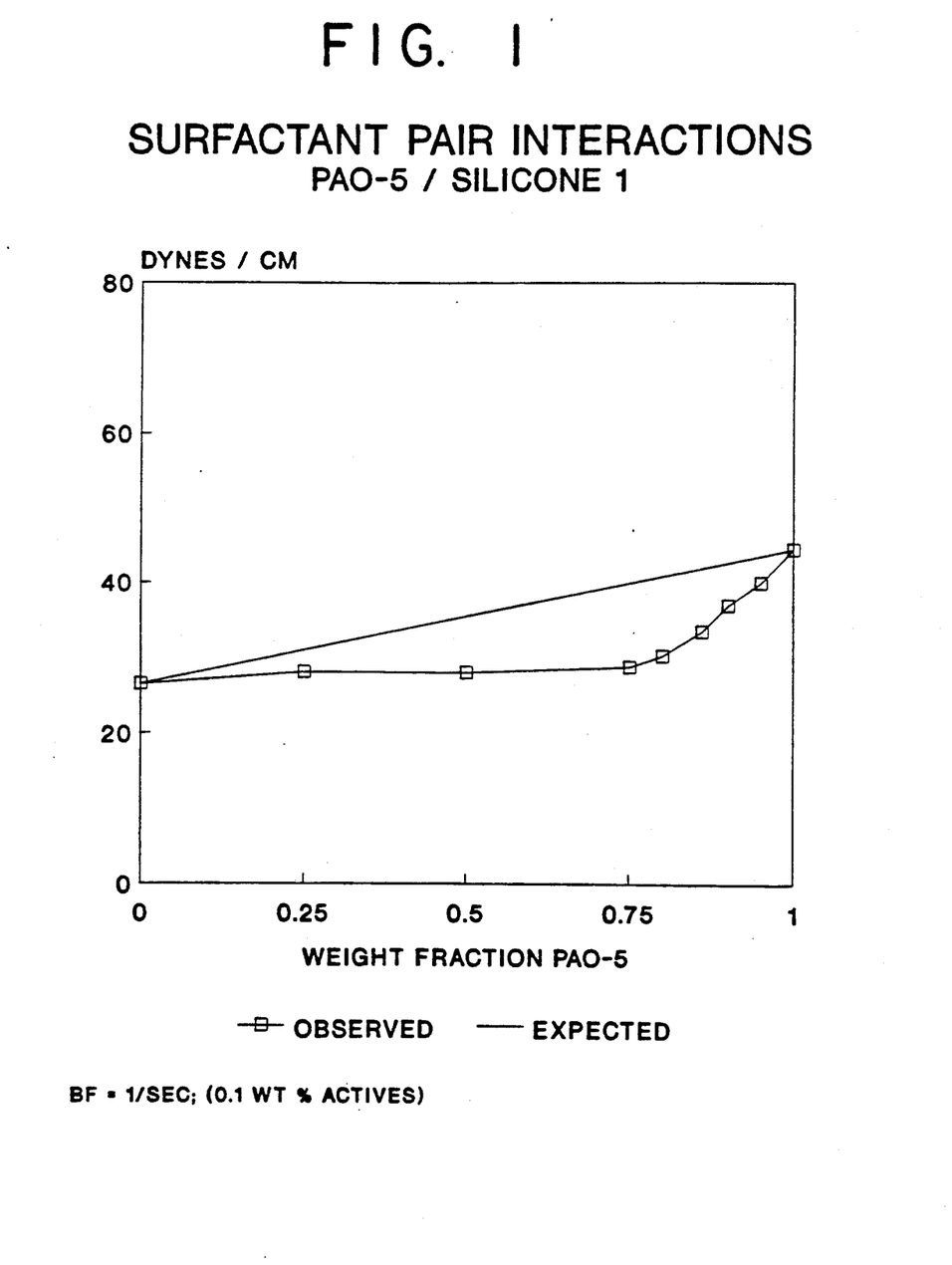
FIGS. 1 to 8 are graphic depictions of the data generated in the Examples.
Figure 2:
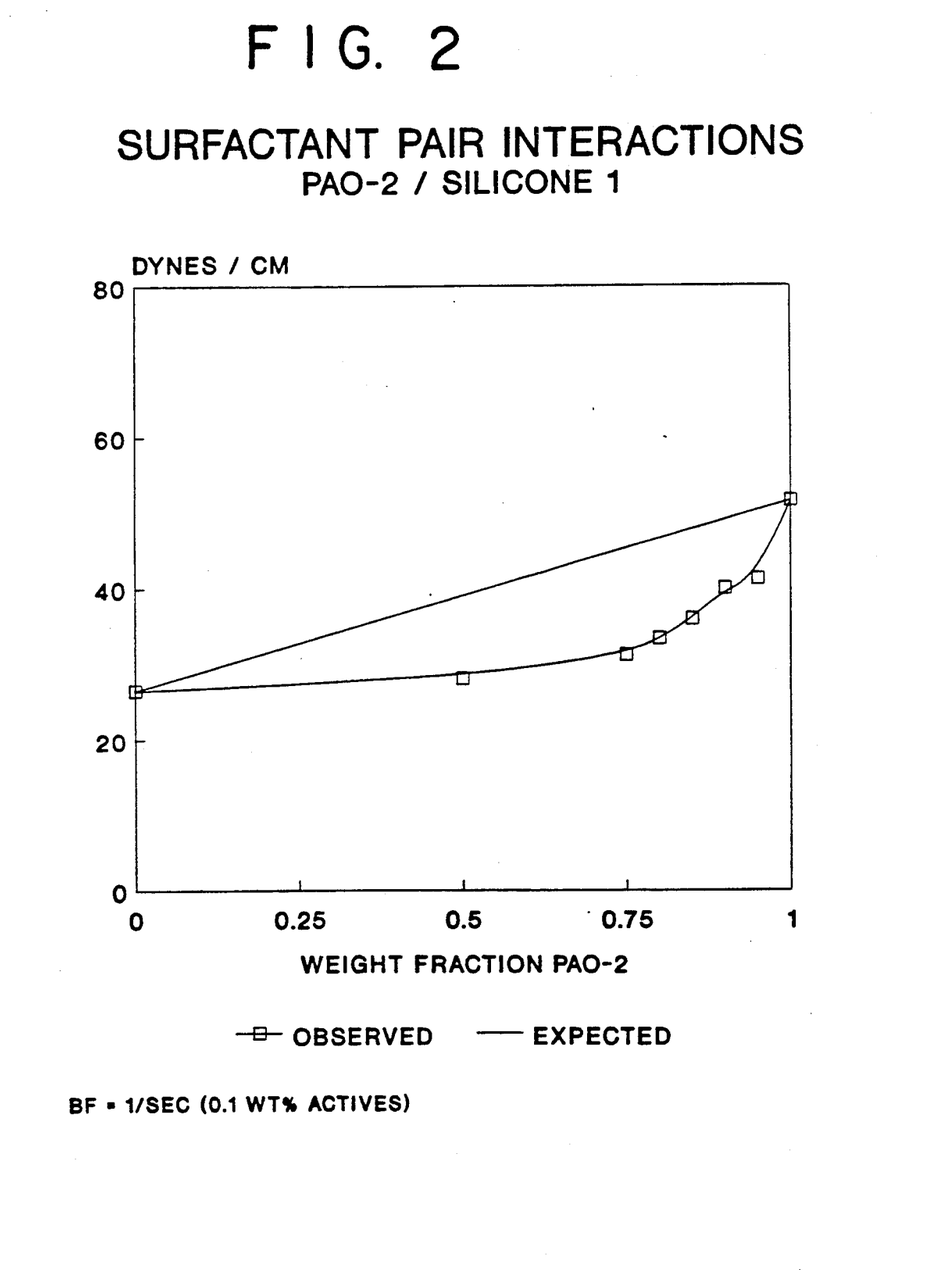
Figure 3:
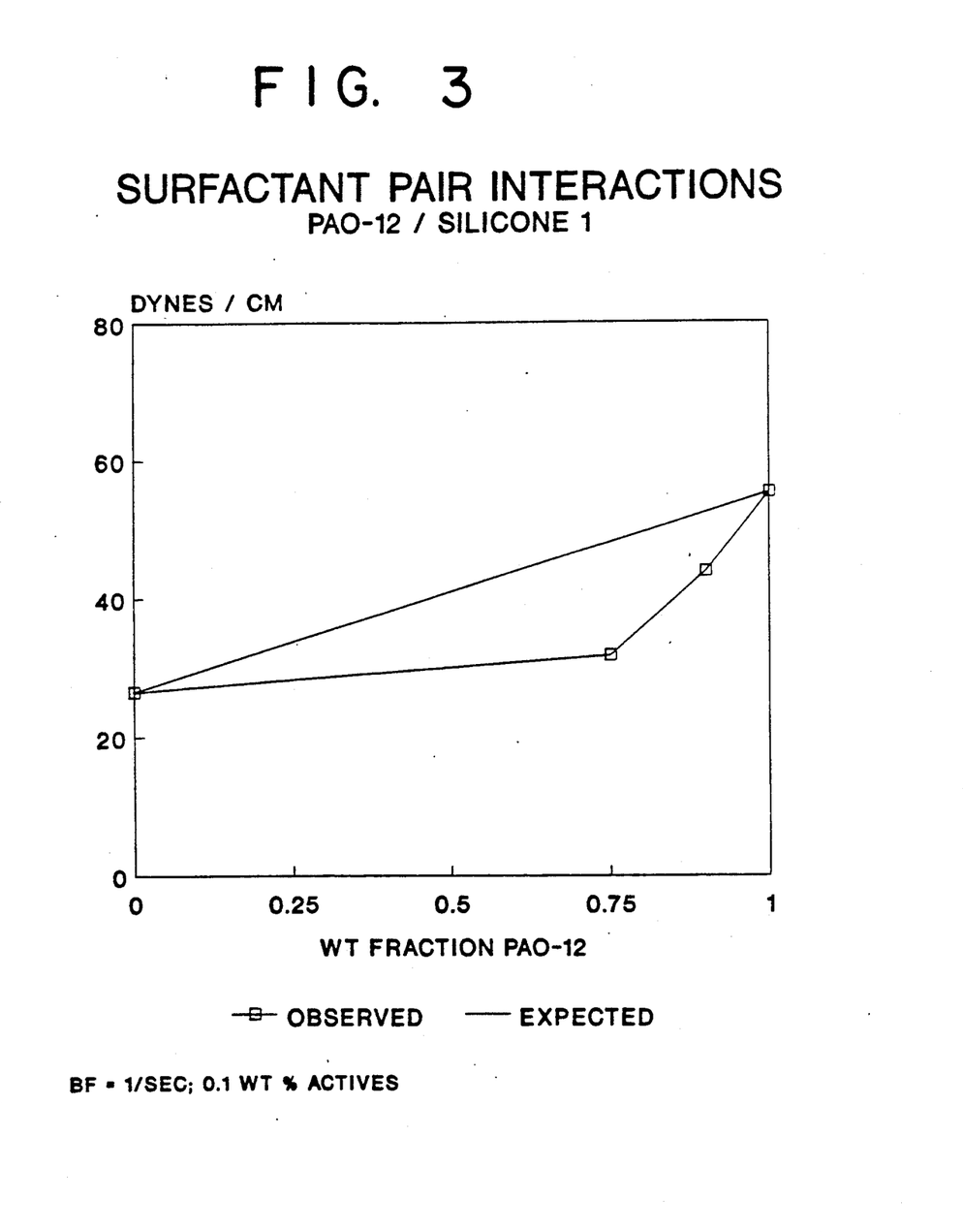
Figure 4:
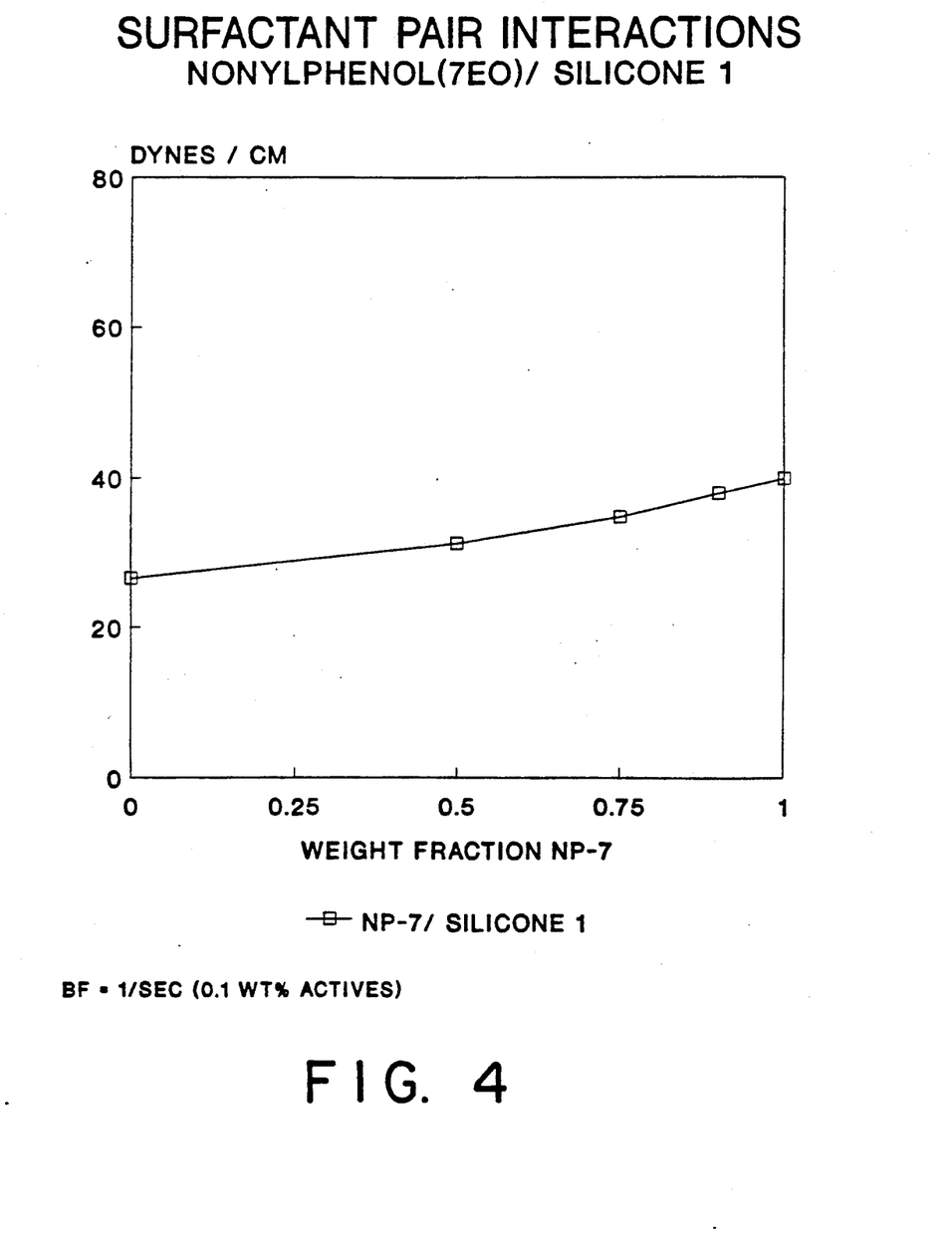

This example demonstrates that PAO/Silicone surfactant pairs display strong non-ideal solution behavior. The dynamic surface tension of surfactant mixtures was determined by the maximum bubble pressure method described earlier in this text. FIG. 1 illustrates the degree of non-ideal behavior observed with mixtures of PAO-5 and Silicone 1. Although the expected interaction profile for these nonionic surfactants is linear, the observed behavior is non-ideal in nature. Similar interactions are observed with other polyalkyleneoxide copolymers such as PAO-2 and PAO-12 (FIGS. 2-3). Also, FIG. 4 demonstrates that mixtures of a nonylphenol ethoxylate with Silicone 1 display linear mixing behavior as expected for nonionic-nonionic pairs.

The degree of interaction for the above surfactant pairs may be expressed as the difference between the expected and the observed values for dynamic surface tension (Table I). A positive value for the change in surface tension ($\Delta Y$) indicates non-ideal behavior. The greater the value for $\Delta Y$ the stronger the interaction. A value of 0 to 2 would indicate little or no interaction, while a value of 4 or greater would indicate moderate to strong non-ideal behavior. Negative results indicate antagonism or a surface tension higher than expected.

TABLE 1

| SURFACTANT PAIR INTERACTIONS | | |
|---|---|---|
| SURFACTANT PAIR | $\Delta\gamma$ 0.75 | $\Delta\gamma$ 0.90 |
| PAO-2/SILICONE 1 | 14.1 | 9.1 |
| PAO-5/SILICONE 1 | 11.1 | 5.6 |
| PAO-12/SILICONE 1 | 16.5 | 8.6 |
| NP-7/SILICONE 1 | 1.8 | 0.6 |
| NP-9/SILICONE 1 | 1.5 | −0.6 |

EXAMPLE 2

Figure 5:
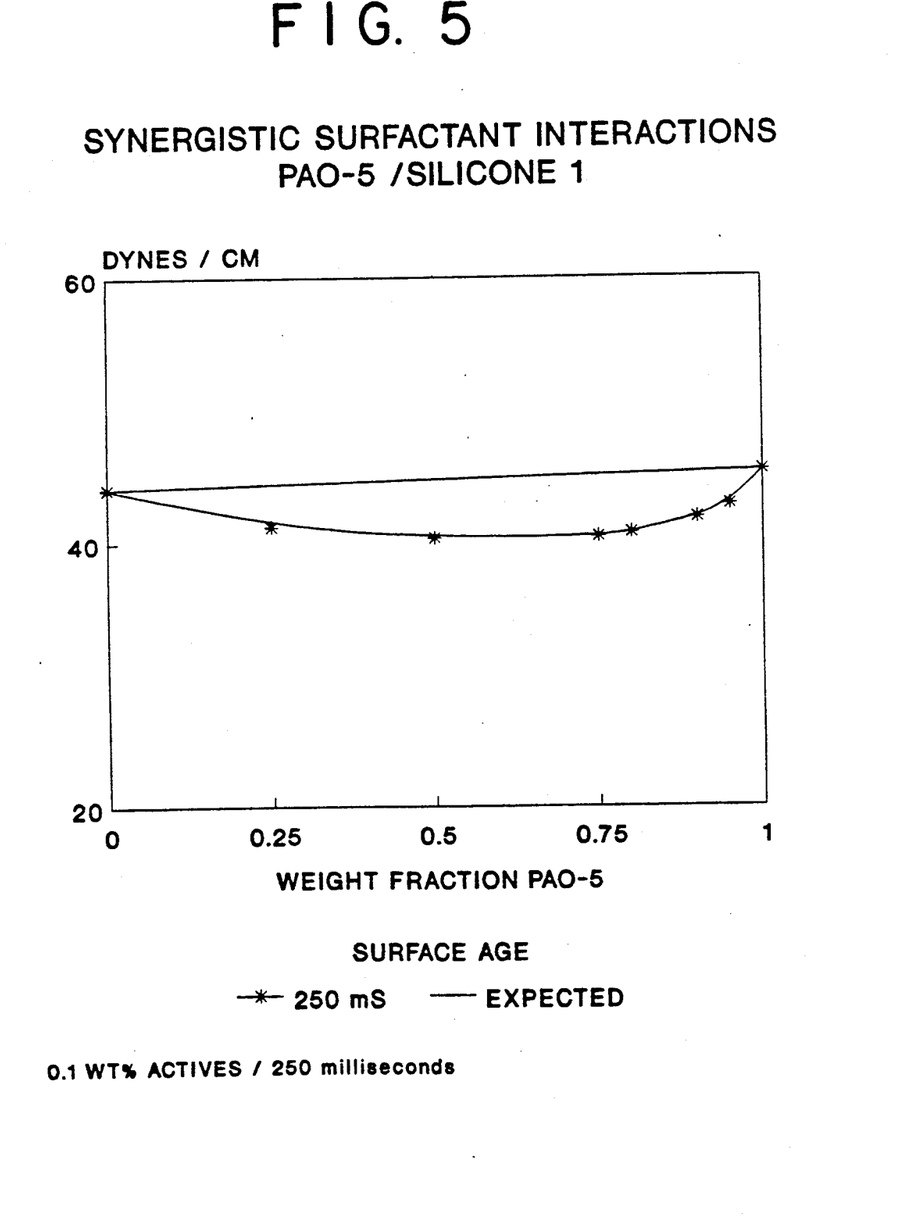
Figure 6:
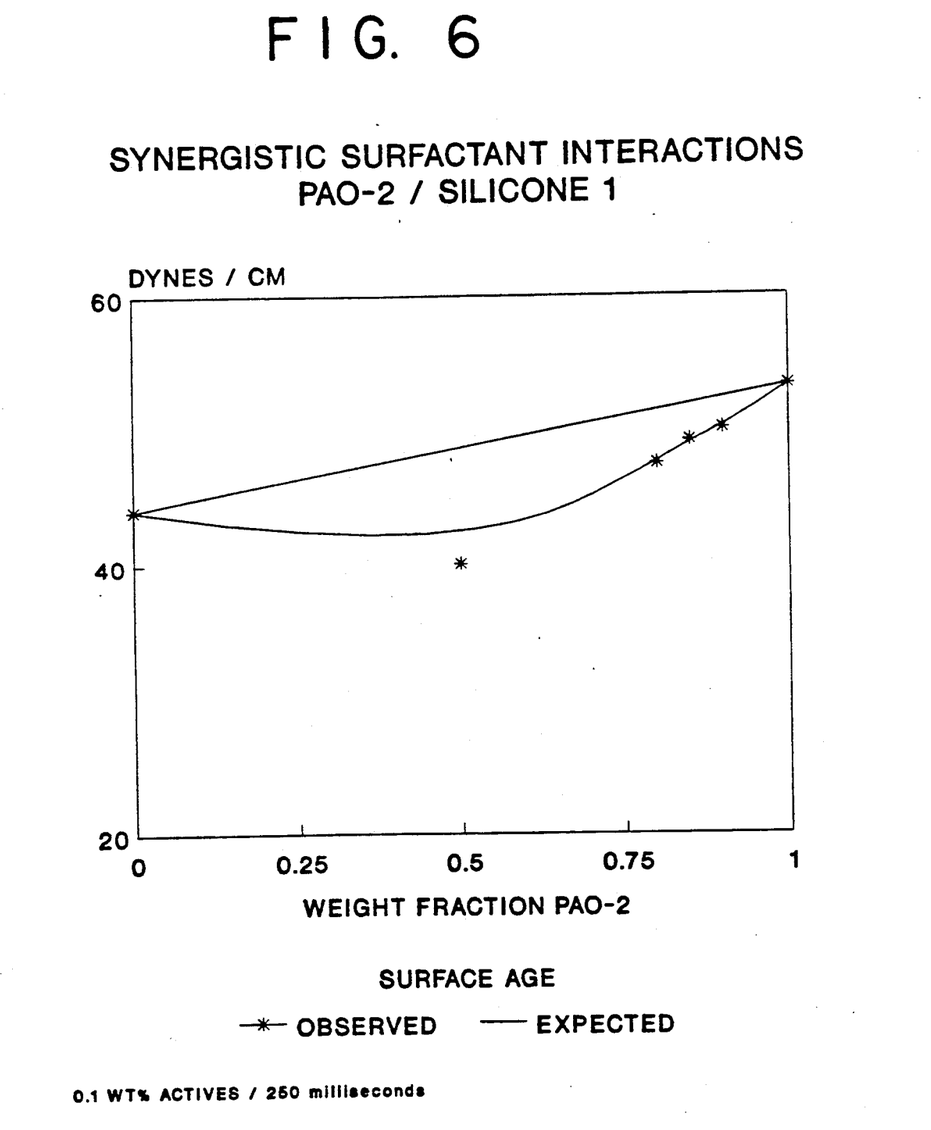

Synergistic interactions are observed for PAO/Silicone surfactants pairs by the dynamic surface tension method described earlier. FIG. 5 demonstrates that mixtures of PAO-5 and Silicone 1 give lower dynamic surface tension values than possible with either of the individual components alone. Similar results are observed for other surfactant pairs such as PAO-2 with Silicone 1 (FIG. 6).

Figure 7:
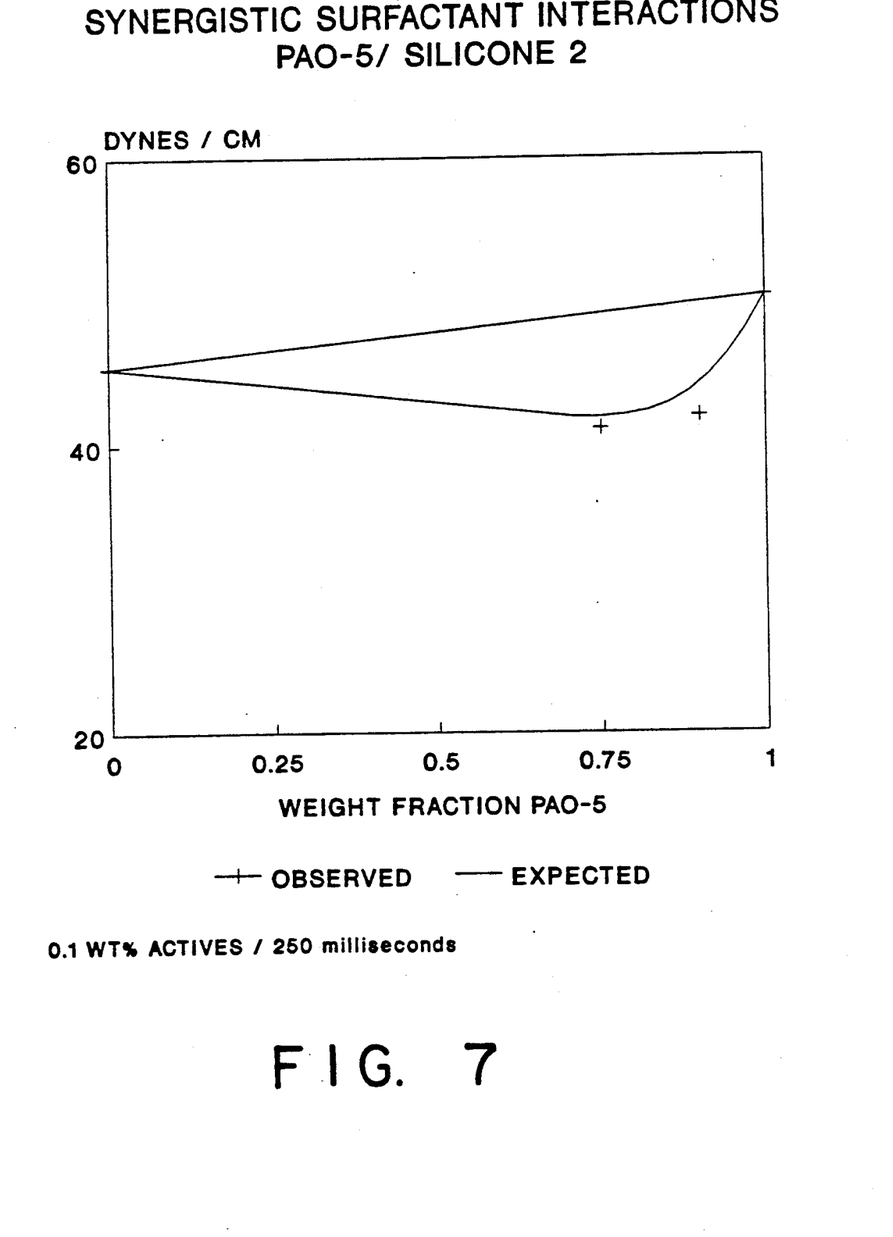
Figure 8:
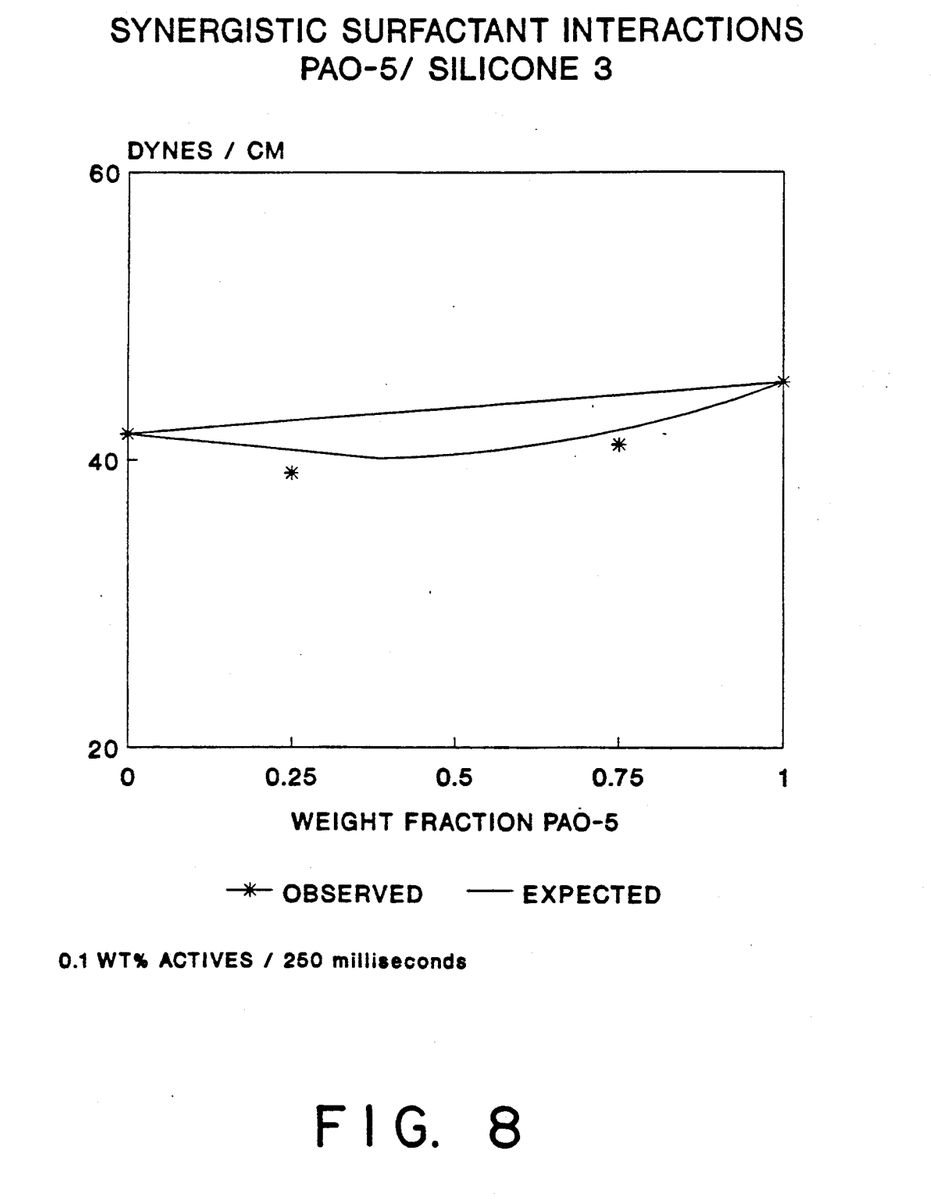

Synergy is also observed for the organosilicone surfactants modified with hydroxy terminated polyethers. This is illustrated, in FIGS. 7 and 8, for mixtures of PAO-5 with Silicone 2 (~8 EO, uncapped) and Silicone 3 (~12 EO, uncapped). Table 2 demonstrates that the degree of synergy is increased with a change from a methyl capped to an uncapped organosilicone surfactant (Compare Silicones 1 and 2).

Also, an increase in synergy is observed with a decrease in the EO content of the silicone (Compare Silicones 2 and 3). Here, as in Example 1, synergy is expressed as the difference between the expected and observed surface tension values.

TABLE 2

SYNERGISTIC INTERACTIONS FOR PAO-5/
SILICONE SURFACTANT PAIRS (a) (b)

| SURFACTANT | (c) $\Delta\gamma 0.75$ | (d) $\Delta\gamma 0.90$ | EO CAP | MOLES EO |
|---|---|---|---|---|
| SILICONE 1 | 4.6 | 3.4 | METHOXY | ~8 |
| SILICONE 2 | 7.9 | 7.8 | HYDROXY | ~8 |
| SILICONE 3 | 3.4 | — | HYDROXY | ~12 |

(a) Surfactant concentration = 0.1 wt %
(b) Surface age 250 milliseconds
(c) Weight fraction PAO-5 = 0.75; Silicone = 0.25
(d) Weight fraction PAO-5 = 0.90; Silicone = 0.10

EXAMPLE 3

The degree of non-ideal behavior is affected by the EO content of the PAO surfactant. Table 3 illustrates the increase in non-ideal behavior with an increase in the WT % EO. Here, the molecular weight of the PO portion is held constant while the EO portion is varied from 20 to 80 wt. %. The interactions are again demonstrated by dynamic surface tension measurements as described earlier.

TABLE 3

THE EFFECT OF EO CONTENT ON NON-IDEAL BEHAVIOR
PAO/SILICONE 1 SURFACTANT PAIRS (a) (d)

| PAO-1 SURFACTANT | ~MW PO PORTION | MOLES EO | $\Delta\gamma 0.75$ (b) | $\Delta\gamma 0.90$ (c) |
|---|---|---|---|---|
| PAO-1 | 950 | 10 | 8.0 | 3.5 |
| PAO-2 | 950 | 50 | 14.1 | 9.1 |
| PAO-3 | 950 | 80 | 14.9 | 11.0 |
| PAO-4 | 1750 | 10 | 2.8 | −1.3 |
| PAO-5 | 1750 | 20 | 11.1 | 5.7 |
| PAO-6 | 1750 | 50 | 12.5 | 7.8 |
| PAO-7 | 1750 | 80 | 16.9 | 13.2 |
| PAO-9 | 3250 | 50 | 7.1 | 5.5 |
| PAO-10 | 3250 | 80 | 20.7 | 16.2 |

(a) Surfactant concentration = 0.1 wt %
(b) Weight fraction PAO = 0.75; Silicone 1 = 0.25
(c) Weight fraction PAO = 0.90; Silicone 1 = 0.10
(d) Surface age = 1000 milliseconds

EXAMPLE 4

Several PAO copolymers were evaluated for the effect of MW on the degree of interaction observed. The EO portion of the PAO was held at 20 and 50 wt % while the overall MW of the PO portion was increased. A decrease in non-ideal behavior is observed, with an increase in molecular weight (Table 4). However, if the EO portion is increased to 80% the effect of the PO molecular weight is obviated and the degree of interaction increases with the total molecular weight of the copolymer.

TABLE 4

THE EFFECT OF PO MOLECULAR WEIGHT
ON NON-IDEAL BEHAVIOR
PAO/SILICONE 1 SURFACTANT PAIRS

| PAO SURFACTANT | ~MW PO PORTION | $\Delta\gamma 0.75$ | $\Delta\gamma 0.90$ |
|---|---|---|---|
| A. 20 WT % EO: | | | |
| PAO-5 | 1750 | 11.1 | 5.7 |
| PAO-8 | 2750 | 7.9 | 4.3 |
| PAO-11 | 5000 | 3.3 | 1.8 |
| B. 50 WT % EO: | | | |
| PAO-2 | 950 | 14.1 | 9.1 |
| PAO-6 | 1750 | 12.4 | 7.8 |
| PAO-9 | 3250 | 7.1 | 5.5 |
| C. 70 WT% EO: | | | |
| PAO-14 | 2250 | 9.8 | 7.9 |
| PAO-15 | 4000 | 16.1 | 8.8 |
| D. 80 WT % EO: | | | |
| PAO-3 | 950 | 14.9 | 11.0 |
| PAO-7 | 1750 | 16.9 | 13.2 |
| PAO-10 | 3250 | 20.7 | 16.2 |

EXAMPLE 5

The effect of PAO conformation on the degree of interaction was also evaluated. The procedure described in Example 1 and the section on Surfactant Performance was used to demonstrate that non-ideal behavior is not limited to EO-PO-EO (ABA) type PAO block copolymers. Other PAO type copolymers that demonstrate non-ideal behavior are block PO-EO-PO (BAB) and random EO/PO copolymers. Table 5 demonstrates that strong non-ideal behavior is observed for these different PAO type copolymers/Silicone 1 surfactant pairs.

TABLE 5

THE EFFECT OF STRUCTURAL CONFORMATION
ON NON-IDEAL BEHAVIOR

| PAO SURFACTANT | STRUCTURAL TYPE | WT % EO | $\Delta\gamma 0.75$ | $\Delta\gamma 0.90$ |
|---|---|---|---|---|
| PAO-2 | ABA | 50 | 14.1 | 9.1 |
| PAO-12 | RANDOM | 50 | 16.5 | 8.6 |
| PAO-13 | BAB | 20 | 9.1 | 4.6 |
| PAO-5 | ABA | 20 | 11.1 | 5.7 |

EXAMPLE 6

Another benefit associated with the types of organosilicone surfactants described in this invention is their wetting ability. Conventional nonionic surfactants such as ethoxylates of octylphenol, nonylphenol or linear alcohols are incapable of effectively wetting hydrophobic surfaces, such as polyester or even a waxy leaf surface. The organosilicone surfactants described in this invention demonstrate excellent wetting properties when used alone. Total wetting is observed since the contact angle of these solutions is close to 0. However, when a cosurfactant is used with these organosilicones at concentrations of >50% of the total surfactant in solution, the spreading character is significantly altered. Total wetting is not achieved and a measurable contact angle is observed.

In this example, a 0.5 wt % solution of a cosurfactant/organosilicone blend (75/25 respectively) is applied to a polyester surface according to the procedure outlined in the experimental section. Table 7 illustrates that PAO copolymers, when used as a cosurfactant for the organosilicones, do not interfere with the spreading character associated with the silicones described in this invention.

TABLE 7

THE EFFECT OF COSURFACTANT ON SPREADING RATIO 0.5 WT %

| SURFACTANT | SPREAD RATIO |
|---|---|
| NONE | 1.0 |
| PAO-5 | 1.7 |
| OP-10 | 2.6 |
| SILICONE 1 | 6.4 |
| SILICONE 2 | 7.8 |
| SILICONE 3 | 4.8 |
| SILICONE 4 | 4.3 |
| PAO-5/SILICONE 1[a] | 12.6 |
| PAO-5/SILICONE 2[a] | 7.8 |
| PAO-5/SILICONE 3[a] | 4.1 |
| PAO-5/SILICONE 4[a] | 7.8 |
| OP-10/SILICON 1[a] | 2.5 |

[a] 0.75/0.25 mixture, 0.5 wt. % total

EXAMPLE 7

Table 8 demonstrates that a wide range of PAO copolymers are acceptable cosurfactants for the organosilicone type surfactants. Blends of Silicone 1 with the PAO surfactants were evaluated for spreading, at 0.1 wt % actives, according to the procedure described in the experimental section. Also, Silicone 1 was applied without a cosurfactant at the appropriate concentrations, as a control. As an example, the 80/20 blend for Silicone 1, in Table represents the concentration of Silicone 1 expected in a 0.1 wt % solution (0.02 wt % Silicone 1). The PAO/Silicone 1 blends were compared to Silicone 1 alone at the corresponding concentrations. Most of the PAO/Silicone 1 blends give equivalent or increased efficiency when compared to the control.

It is also demonstrated that a reduction in efficiency is observed only at the higher molecular weight and low wt % EO range. PAO-11 is an example of the type of PAO cosurfactant where a reduction in spreading efficiency is observed.

TABLE 8

THE EFFECT OF PAO TYPE ON SPREADING EFFICACY OF SILICONE 1 (0.1 WT % TOTAL)

| PAO SURFACTANT | MW | WT % EO | WT % SILICONE 1 SPREAD RATIO | | |
|---|---|---|---|---|---|
| | | | 0.02 WT % | 0.025 WT % | 0.04 WT % |
| NONE 1 | N/A | N/A | 3.4 | 5.2 | 7.3 |
| PAO-1 | 1100 | 10 | 3.2 | 5.2 | 8.3 |
| PAO-2 | 1900 | 50 | 3.8 | 5.2 | 8.0 |
| PAO-3 | 5000 | 80 | 3.3 | 5.8 | 8.5 |
| PAO-5 | 2500 | 20 | 6.2 | N/A | 11.4 |
| PAO-6 | 3400 | 50 | 3.2 | 5.1 | 7.9 |
| PAO-7 | 8350 | 80 | 3.2 | 5.3 | 8.2 |
| PAO-8 | 3650 | 20 | 3.9 | 4.8 | 7.9 |
| PAO-11 | 5000 | 20 | 1.9 | 1.9 | 4.8 |

EXAMPLE 8

This experiment was to determine if spreading is affected by a high PAO content. Spreading does appear to be diminished by the presence of PAO-5 at a ratio of >24/1. All of the test points are done at a total surfactant concentration that will deliver 0.1 wt % Silicone 1.

TABLE 9

SPREAD FOR SILWET SURFACTANT SILICONE 1/PAO-5 BLENDS

| SURFACTANT BLEND | SURFACTANT BLEND RATIO | SPREAD RATIO |
|---|---|---|
| WATER | — | 1.0 |
| SILICONE 1 (0.1%) | — | 13.1 |
| PAO-5 (10%) | — | 2.6 |
| PAO-5 (9.9%) SILICONE 1 (0.1%) | 99/1 | 2.6 |
| PAO-5 (4.9%) SILICONE 1 (0.1%) | 49/1 | 4.3 |
| PAO-5 (2.4%) SILICONE 1 (0.1%) | 24/1 | 11.4 |
| PAO-5 (0.9%) SILICONE 1 (0.1%) | 9/1 | 14.8 |

EXAMPLE 9

A field trial was run where Roundup TM by Monsanto Company was sprayed on velvet leaf, morning glory and johnson grass weeds at 14 ounces per 20 gallons of water (manufacturers recommended procedure). The comparison is made with and without the surfactant mixture. After 33 days the rate of control of the weeds (e.g. the kill rate) was measured. The use of the surfactant blend improved the efficiency of the herbicide as shown in Table 10.

TABLE 10

DOSE RESPONSE ROUNDUP

| PAO-5/SILICONE 1 (% v/v) | 33 DAT | | |
|---|---|---|---|
| | MORNING GLORY | VELVET LEAF | JOHNSON GRASS |
| 0 | 50.0 | 50.0 | 66.7 |
| 0.10 | 58.3 | 56.7 | 83.3 |
| 0.25 | 56.7 | 53.3 | 73.3 |
| 0.50 | 53.3 | 66.7 | 76.7 |

We claim:

1. A surfactant blend comprising 1 to 99 weight percent organosilicone surfactant and 1 to 99 weight percent polyalkyleneoxide copolymer wherein (a): the organosilicone surfactant is of the general formula:

$$MD'_xM \quad (I)$$

wherein:
M is $Me_3SiO_{\frac{1}{2}}$
D' is MeRSiO,
Me is $CH_3$
R is $C_nH_{2n}O(C_2H_4O)_a(C_3H_6O)_bR'$, n is from 2 to 4,
a is 3 to 25,
b is from 0 to 25,
R' is hydrogen, an alkyl group having 1 to 4 carbon atoms, or an alkyl ester group wherein the alkyl group of the ester has 1 to 4 carbon atoms,
x is 1 to 5; and (b): the polyalkyleneoxide copolymer is of the general formula:

$$R''O\text{-}(C_2H_4O)_c(C_3HO)_d\text{—}R'' \qquad (II)$$

wherein:
c is 0 to 300,
d is 1 to 300, and
R" is hydrogen or an alkyl group having 1 to 4 carbon atoms; and wherein the organosilicone surfactant is soluble in the polyalkyleneoxide copolymer.

2. The blend of claim 1 wherein the organosilicone compound is one in which n is 3, a is 3 to 15, b is 0 to 15, x is 1 and R' is hydrogen or a methyl group.

3. The blend of claim 1 wherein the polyalkyleneoxide copolymer is one in which c is 20 to 100, d is 20 to 100 and R" is hydrogen.

4. The blend of claim 2 wherein the polyalkyleneoxide copolymer is one in which c is 20 to 100, d is 20 to 100 and R" is hydrogen.

5. The blend of claim 1 wherein the 1 to 50 weight percent is the organosilicon compound and 50 to 99 weight percent is the polyalkyleneoxide copolymer.

* * * * *